(12) United States Patent
Leger et al.

(10) Patent No.: US 8,389,783 B2
(45) Date of Patent: Mar. 5, 2013

(54) PROCESS FOR HYDROGENATION OF AN AROMATIC FEEDSTOCK THAT AS CATALYST USES A SUSPENSION OF METAL NANOPARTICLES CONTAINING A NITROGEN-CONTAINING LIGAND IN AN IONIC LIQUID

(75) Inventors: Bastien Leger, Charleville-Mezieres (FR); Alain Roucoux, Thorigne-Fouillard (FR); Helene Olivier-Bourbigou, Saint Genis-Laval (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 339 days.

(21) Appl. No.: 12/597,260

(22) PCT Filed: Apr. 14, 2008

(86) PCT No.: PCT/FR2008/000523
§ 371 (c)(1),
(2), (4) Date: Apr. 16, 2010

(87) PCT Pub. No.: WO2008/145835
PCT Pub. Date: Dec. 4, 2008

(65) Prior Publication Data
US 2010/0228064 A1    Sep. 9, 2010

(30) Foreign Application Priority Data
Apr. 26, 2007 (FR) .................................. 07 03115

(51) Int. Cl.
*C07C 5/10* (2006.01)
(52) U.S. Cl. ...................................... 585/269; 585/265
(58) Field of Classification Search ............... None
See application file for complete search history.

(56) References Cited

U.S. PATENT DOCUMENTS
5,852,130 A    12/1998 Mussmann et al.

FOREIGN PATENT DOCUMENTS
EP    0 748 653 A1    12/1996

OTHER PUBLICATIONS

International Search Report of PCT/FR2008/000523 (Dec. 16, 2008).
G. S. Fonseca et al., "The Use of Imidazolium Ionic Liquids for the Formation and Stabilization of $Ir^0$ and $Rh^0$ Nanoparticles: Efficient Catalysts for the Hydrogenation of Arenes", Chem. Eur. J., vol. 9 (2003) pp. 3263-3269.
E. Ramirez et al., "Influence of Organic Ligands on the Stabilization of Palladium Nanoparticles", Journal of Organometallic Chemistry, vol. 689 (2004) pp. 4601-4610.
B. Leger et al., "Synthesis of Bipyridine-Stabilized Rhodium Nanoparticles in Non-Aqueous Ionic Liquids: A New Efficient Approach for Arene Hydrogenation with Nanocatalysts", Adv. Synth. Catal., vol. 350 (2008) pp. 153-159.
U. R. Pillai et al., "Phenanthroline-Stabilized Palladium Nanoparticles in Polyethylene Glycol—An Active and Recyclable Catalyst System for the Selective Hydrogenation of Olefins Using Molecular Hydrogen", Journal of Molecular Catalysis A: Chemical, vol. 222 (2004) pp. 153-158.
J. Huang et al., "Hydrogenation of Olefins Using Ligand-Stabilized Palladium Nanoparticles in an Ionic Liquid", Chem. Commun., (2003) pp. 1654-1655.

*Primary Examiner* — Tam M Nguyen
(74) *Attorney, Agent, or Firm* — Millen, White, Zelano & Branigan, P.C.

(57) ABSTRACT

This invention describes a process for hydrogenation of an aromatic feedstock that as a catalytic composition uses a suspension of metal nanoparticles of a mean size of between 1 and 20 nanometers in at least one non-aqueous ionic liquid, whereby said suspension also contains at least one nitrogen-containing ligand, in which said metal nanoparticles comprise a transition metal in the zero-valence state, whereby the transition metal is selected from the groups 8, 9, 10 and 11 of the periodic table and in which said nitrogen-containing ligand comprises 1 to n nitrogen atoms, whereby n is an integer of between 1 and 20.

10 Claims, No Drawings

PROCESS FOR HYDROGENATION OF AN AROMATIC FEEDSTOCK THAT AS CATALYST USES A SUSPENSION OF METAL NANOPARTICLES CONTAINING A NITROGEN-CONTAINING LIGAND IN AN IONIC LIQUID

FIELD OF THE INVENTION

This invention describes a process for hydrogenation of an aromatic feedstock that as a catalytic composition uses a suspension of metal nanoparticles of a mean size of between 1 and 20 nanometers in at least one non-aqueous ionic liquid, whereby said suspension also contains at least one nitrogen-containing ligand, in which said metal nanoparticles comprise a transition metal in the zero-valence state, whereby the transition metal is selected from the groups 8, 9, 10 and 11 of the periodic table and in which said nitrogen-containing ligand comprises 1 to n nitrogen atoms, whereby n is an integer of between 1 and 20.

PRIOR ART

The use of nanoparticles of transition metals for catalyzing the hydrogenation of unsaturated compounds is currently experiencing a significant resurgence as it is described in the literature. These catalysts that generally comprise a transition metal in the zero-valence state are very advantageous due to their unique properties, such as, for example, their large specific surface area that imparts to them excellent reactivity and good selectivity even under mild reaction conditions. One of the primary characteristics of these particles is their small size that is generally between 1 and 3 nm.

Several methods for synthesis of nanoparticles are described: electrochemical, sonochemical, condensation of metal vapors, . . . but the most commonly used and the most simple implements a chemical reduction of transition metal salts [see: A. Roucoux, J. Schulz, H. Patin, Chem. Rev. 2002, 102, 3757]. The size of the particles may depend, however, on the reduction conditions (nature of the reducing agents, concentration, solvent, . . . ). Different types of reducing agents have been used, such as hydrides or metal salts, molecular hydrogen, carbon monoxide, or else organic compounds that can be oxidized, such as reducing alcohols. The reduction can be done from the corresponding metal salt or else by reaction of an organometallic precursor with molecular hydrogen by ligand displacement.

The nanoparticles of the transition metals are naturally not very stable and have a strong tendency to become agglomerated, thus losing their nanoscopic nature. This aggregation usually brings about the loss of properties linked to their colloidal state and is generally reflected in catalysis by a loss of activity and reproducibility problems. The stabilization of the metal nanoparticles and therefore the preservation of their finely divided nature is a basic stage during their synthesis.

Several types of stabilization have been taken into consideration:

(i) Electrostatic stabilization. This is a Coulomb repulsion that is generated by the use of ionic compounds (chloride, carboxylates or polyoxoanions) that are adsorbed on the surface of the nanoparticles and that generate a double electric layer because of the presence of the counter-ion, (ii) The steric stabilization that is based on the use of ligands or macromolecules such as polymers or oligomers, (iii) The combination of these last two stabilization methods, namely the electrosteric stabilization (for example with the use of ionic surfactants or ligands).

The catalytic activity and the selectivity of these nanoparticles in solution depends not only on the relative abundance of the different active sites but also on the concentration and the type of stabilizers that are present in the medium.

However, if the nanoparticles of the transition metals have numerous advantages in catalysis, these catalysts can also generate certain drawbacks:

In general, they are not very stable thermally and can rapidly agglomerate,

The separation of the soluble catalyst from the products of the reaction can pose a problem.

The combination of a ligand and an ionic liquid has been sparingly described for the synthesis and the stabilization of nanoparticles. However, the presence of the ligand can have a double advantage: "to solubilize" the active radicals (nanoparticles) in the non-aqueous ionic liquids and to modulate their reactivity (selectivity and activity). Nanoparticles that are stable in solution are then obtained. The combination of a ligand, a metal and an ionic liquid can provide a noteworthy synergetic effect that makes it possible to enhance the catalytic activity of these systems and to improve their stability (service life). Furthermore, their separation from the products of the reaction and their recycling can be done by simple decanting in a two-phase liquid-liquid catalysis process and/or by liquid-liquid extraction.

The studies concern the combination of a metal compound, a nitrogen-containing ligand, and a non-aqueous ionic liquid as a catalytic composition, and it has now been found that the use of such a combination made it possible to avoid the drawbacks cited above, while improving the catalytic activity and the stability of the catalytic system and by making possible a very simple separation of the reaction products as well as the recycling of said catalytic composition.

OBJECT OF THE INVENTION

This invention describes a process for hydrogenation of an aromatic feedstock that as a catalytic composition uses a suspension of metal nanoparticles with a mean size of between 1 and 20 nanometers in at least one non-aqueous ionic liquid, whereby said suspension also contains at least one nitrogen-containing ligand, in which said metal nanoparticles comprise a transition metal in the zero-valence state, whereby the transition metal is selected from the groups 8, 9, 10 and 11 of the periodic table and in which said nitrogen-containing ligand comprises 1 to n nitrogen atoms, whereby n is an integer that is between 1 and 20.

DETAILED DESCRIPTION OF THE INVENTION

The invention relates to a process for hydrogenation of an aromatic feedstock that as a catalytic composition uses a suspension of metal nanoparticles in at least one non-aqueous ionic liquid.

Nanoparticles are defined as particles whose size can vary by several angstroms to several tens of nanometers.

The size of the nanoparticles is determined by all of the methods that are known to one skilled in the art.

The transmission electron microscopy (TEM) makes it possible, for example, to characterize the metal nanoparticles and to obtain direct visual information on the size, the shape, the dispersion, the structure and the morphology of the nanoparticles.

According to the invention, the mean size of the nanoparticles is between 1 and 20 nanometers. Preferably, the mean size of the nanoparticles is between 1 and 10 nanometers. The mean size of the particles according to the invention is determined from the measurement of a lot of 400 particles per sample using counting software based on shape recognition.

Process for the Preparation of the Suspension of Metal Nanoparticles in an Ionic Liquid.

The suspension of metal nanoparticles in an ionic liquid, used as a catalytic composition in the hydrogenation process according to the invention, is obtained by chemical reaction, by a simple bringing into contact, followed by stirring, of a metal precursor, a reducing agent, at least one ionic liquid and at least one nitrogen-containing ligand, optionally in the presence of an organic solvent, whereby the addition of different components can be done in any order.

Preferably, the addition of the nitrogen-containing ligand can be done in a second stage that follows a first stage for bringing into contact the metal precursor, the reducing agent and the ionic liquid. In this case, the addition of the ligand is done after the metal precursor reacts with the reducing agent in the presence of the ionic liquid and optionally the organic solvent.

The metal precursors can be compounds of transition metals that are selected from the groups 8, 9, 10 and 11 of the periodic table, for example metal salts such as halides (for example, chlorides, bromides or else iodides), acetates, sulfates, carboxylates, phenates and acetylacetonates. It is also possible to use organometallic complexes or oxides.

The reducing agents can be metals such as zinc, aluminum, lithium, hydrides or metal salts such as sodium borohydride, potassium borohydride, and sodium citrate. The reduction can also be carried out by molecular hydrogen or carbon monoxide. It is also possible to use organic compounds such as ascorbic acid or hydrazine, or else organic solvents that can be oxidized, such as alcoholic derivatives like methanol, ethanol, 2-propanol, ethylene glycol or propylene glycol.

The non-aqueous ionic liquids and the nitrogen-containing ligands that are selected from the group that is formed by the compounds comprising 1 to n nitrogen atoms, whereby n is an integer between 1 and 20, are defined later in the description.

The optional organic solvent is preferably selected from among aromatic hydrocarbons, hydrocarbon compounds, halogenated hydrocarbon compounds, ethers and alcohols.

When one organic solvent is used, it can be eliminated at the end of the reaction of the suspension of metal nanoparticles in the ionic liquid by all methods that are known to one skilled in the art and preferably by evaporation under reduced pressure.

Said metal nanoparticle suspension in the ionic liquid that is thus obtained is then used just as is after evaporation of the solvent in the process for hydrogenation of the aromatic compounds according to the invention.

When the organic solvent that is used is an aromatic solvent, it preferably will be eliminated at the end of synthesis to prevent it from participating in the hydrogenation reaction for which the suspension of nanoparticles is described according to the invention.

Said metal nanoparticle suspension in the ionic liquid is prepared under the following operating conditions:

The temperature of the reaction is between −20° C. and 200° C. and preferably between −10° C. and 100° C.

The pressure is between 1 and 80 bar and preferably between 1 and 50 bar.

The molar ratio between the reducing agent and the metal precursor is between 1 and 50 and preferably between 1 and 5.

It should be noted that in the case of organic solvents being used as reducing agents, the quantity of solvent and therefore of reducing agent is not limited.

The molar ratio between the ligand and the metal precursor metal is between 0.001 and 100 and preferably between 0.01 and 10.

The metal concentration in the ionic liquid is between $1.9 \times 10^{-5}$ and 19 mol·L$^{-1}$ and preferably between $1.9 \times 10^{-5}$ and 1.9 mol·L$^{-1}$.

The suspension of metal nanoparticles in the ionic liquid above will now be described more specifically within the framework of its use as a catalytic composition for a process for hydrogenation of aromatic feedstocks according to the invention. Said catalytic composition comprises three characteristic elements: metal, ligand and non-aqueous ionic liquid.

The Metal

According to the invention, the transition metal is selected from the group that is formed by the elements of groups 8, 9, 10 and 11 according to the new notation of the periodic table (Handbook of Chemistry and Physics, 76$^{th}$ Edition, 1995-1996).

According to one preferred embodiment, the metal is selected from among rhodium, ruthenium, iridium, nickel, palladium, and platinum, by themselves or in a mixture.

According to one very preferred embodiment, the metal is selected from among rhodium, ruthenium and iridium, by themselves or in a mixture.

According to an even more preferred embodiment, the metal is rhodium.

According to another even more preferred embodiment, the metal is ruthenium.

Palladium can be used in the process for hydrogenation of an aromatic feedstock according to the invention but results in less advantageous performances, in particular when it is used with a nitrogen-containing ligand of the family of phenanthrolines. Thus, preferably, the combination of the palladium and nitrogen-containing ligand of the family of phenanthrolines is not used in the process according to the invention.

Said catalytic composition also comprises at least one nitrogen-containing ligand.

The Ligand

According to the invention, the nitrogen-containing ligand is selected from the group that is formed by the compounds that comprise 1 to n nitrogen atoms, whereby n is an integer of between 1 and 20, and preferably between 1 and 10, and even more preferably between 1 and 7.

According to a preferred embodiment, the nitrogen-containing ligand is selected from the group that is formed, more particularly, by linear compounds, non-aromatic cyclic compounds, non-condensed aromatic compounds, and condensed aromatic compounds.

In the embodiment where the nitrogen-containing ligand is selected from among the linear compounds, the nitrogen-containing ligand is preferably selected from among the families of alkylamines, diamines, polyamines and polyethyleneimines, whose general formulas are shown below:

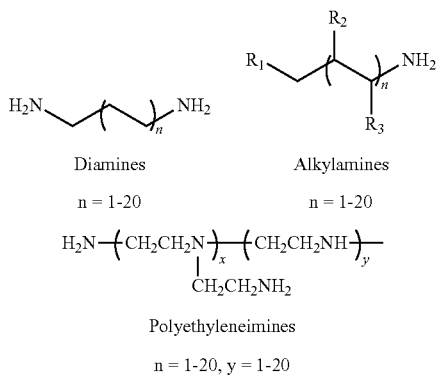

Diamines
n = 1-20

Alkylamines
n = 1-20

Polyethyleneimines
n = 1-20, y = 1-20

In the embodiment where the nitrogen-containing ligand is selected from among the non-aromatic cyclic compounds, the nitrogen-containing ligand is preferably selected from among the families of bipiperidines and substituted bipiperidines, polyazacycloalkanes, oxazolidines, and substituted oxazolidines, and oxazolines and substituted oxazolines whose general formulas are shown below:

The substituted bipiperidines, whereby the amine group —NH can occupy the positions 2-2', 3-3' and 4-4'.

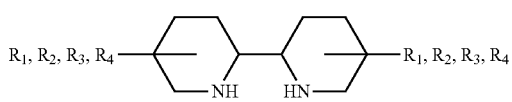

The polyazacycloalkanes with n=[1; 100], p=[1; 20], m=[1; 10], x=[1; 100], and y=[1; 100]

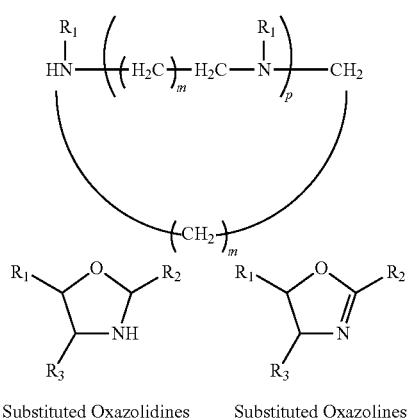

Substituted Oxazolidines    Substituted Oxazolines

In the embodiment where the nitrogen-containing ligand is selected from among the non-condensed aromatic compounds, the nitrogen-containing ligand is preferably selected from among the families of pyridines and substituted pyridines, bipyridines and substituted bipyridines, bis(2-pyridyl)alkanes and substituted bis(2-pyridyl)alkanes, bis(3-pyridyl)alkanes and substituted bis(3-pyridyl)alkanes, bis(4-pyridyl)alkanes and substituted bis(4-pyridyl)alkanes, bis(2-pyridinyl)alkanes and substituted bis(2-pyridinyl)alkanes, pyrazines and substituted pyrazines, and triazines and substituted triazines, whose general formulas are shown below:

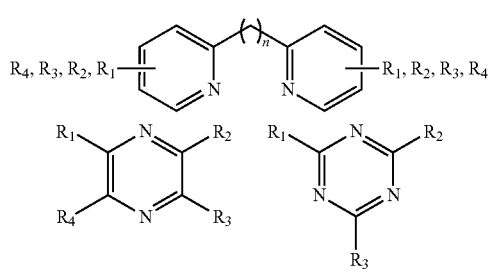

Substituted Pyridines

Substituted bipyridines, whereby the nitrogen atoms can occupy the positions 2-2', 3-3' and 4-4'.

Substituted bis(2-pyridyl)alkanes, whereby the nitrogen atoms can occupy the positions 2-2', 3-3', and 4-4', and n is between 1 and 20.

Substituted Pyrazines    Substituted Triazines

When the nitrogen-containing ligand is selected from among the non-condensed aromatic compounds of the family of substituted pyrazines, preferably, the nitrogen-containing ligand is tetra-2-pyridinyl-pyrazine or TPPZ or the bis-pyridyl-pyrazine of general formulas that are shown below:

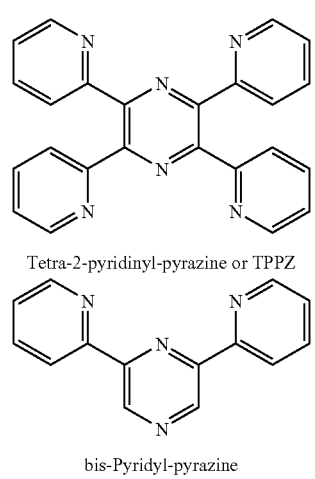

Tetra-2-pyridinyl-pyrazine or TPPZ bis-Pyridyl-pyrazine

More preferably, the nitrogen-containing ligand is tetra-2-pyridinyl-pyrazine or TPPZ.

When the nitrogen-containing ligand is selected from among the non-condensed aromatic compounds of the family of substituted triazines, preferably, the nitrogen-containing ligand is 2,4,6-tris-(2-pyridyl)-s-triazine or TPST of the general formula that is shown below:

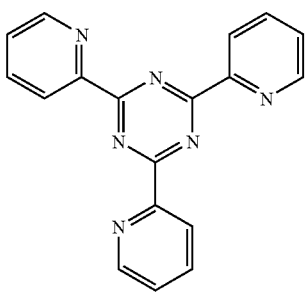

In the embodiment where the nitrogen-containing ligand is selected from among the condensed aromatic compounds, the nitrogen-containing ligand is preferably selected from among the families of naphpyridines and substituted naphpyridines, quinolines and substituted quinolines, biquinolines and substituted biquinolines, isoquinolines and substituted isoquinolines, dibenzopyridines and substituted dibenzopyridines, phenazines and substituted phenazines, phenanthridines and substituted phenanthridines, and phenanthrolines and substituted phenanthrolines, whose general formulas are shown below:

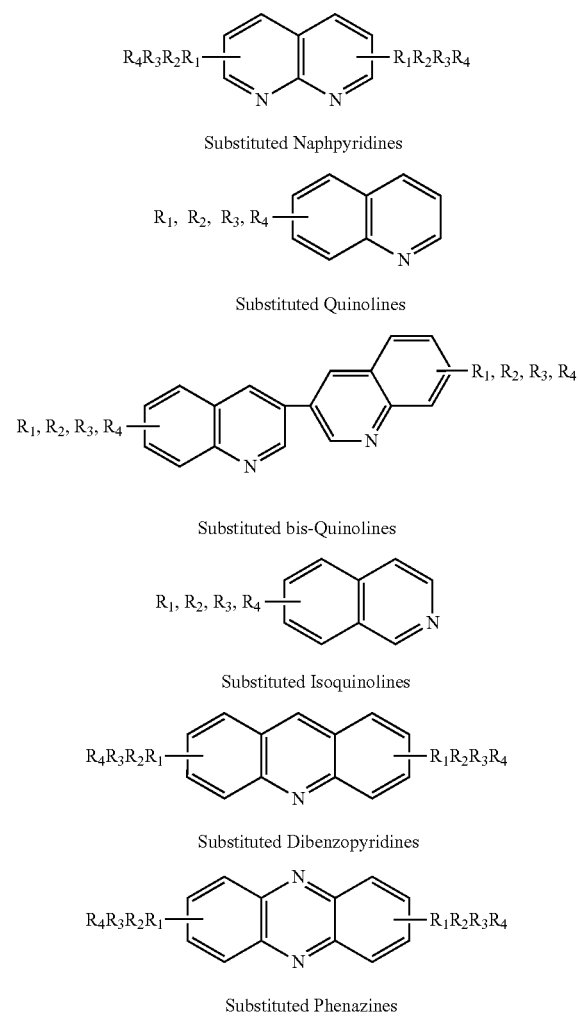

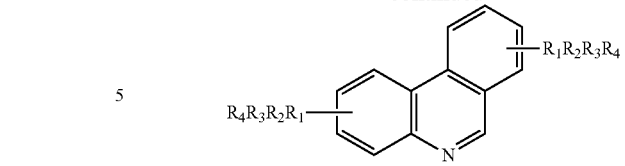

Substituted Phenanthridines

The phenanthrolines, whereby the nitrogen atoms can occupy the positions 1-10, 1-7, and 4-7. However when the transition metal is palladium, the phenanthrolines are excluded.

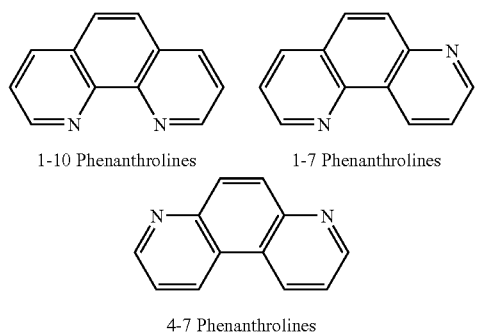

In all of the general formulas of the compounds above, the groups R1, R2, R3 and R4 can be identical or different. The groups R1, R2, R3 and R4 are advantageously alkyl radicals, cycloalkyl radicals, aryl radicals or aralkyl radicals, comprising 1 to 10 carbon atoms. They can also comprise a functional group, such as, for example, an amine, a cyclic amine, a nitrogen-containing heterocycle, an ester, an acid, an alcohol, a quaternary ammonium, an imidazolium cation, a pyrrolidinium cation, a pyridinium cation, a quaternary phosphonium, a sulfonium, a sulfonate or a phosphonate.

Said catalytic composition also comprises a non-aqueous ionic liquid.

The Non-Aqueous Ionic Liquids:

The non-aqueous ionic liquids are generally compounds that are represented by the general formula $Q^+A^-$ and are prepared according to preparation methods that are known to one skilled in the art.

The $A^-$ anions are preferably selected from among the following anions: halides, nitrates, sulfates, alkylsulfates, phosphates, alkylphosphates, acetates, haloacetates, tetrafluoroborates, tetrachloroborates, hexafluorophosphates, trifluoro-tris-(pentafluoroethyl)phosphates, hexafluoroantimonates, fluorosulfonates, alkylsulfonates, such as, for example, methylsulfonate; perfluoroalkylsulfonate anions, such as, for example, trifluoromethylsulfonate; bis(perfluoroalkylsulfonyl)amide anions, such as, for' example, the bis-trifluoromethylsulfonyl amide of formula $N(CF_3SO_2)_2^-$, the tris-trifluoromethylsulfonyl methylide of formula $C(CF_3SO_2)_3^-$, the bis-trifluoromethylsulfonyl methylide of formula $HC(CF_3SO_2)_3^-$; the arenesulfonate anions, optionally substituted by halogen or haloalkyl groups; the tetraphenylborate anion, and the tetraphenylborate anions whose aromatic cores are substituted; the tetra-(trifluoroacetoxy)-borate anion, the bis-(oxalato)-borate anion, the dicyanamide anion, the tricyanomethylide anion, as well as the chloroaluminate anions, the chlorozincate anions, and the chloroferrate anions.

The Q+ cations are preferably selected from among the group that is formed by phosphoniums, ammoniums, guanidiniums and sulfoniums.

In all of the general formulas that are represented below, the groups $R^1$, $R^2$, $R^3$, $R^4$, $R^5$ and $R^6$ advantageously represent hydrogen (with the exception of the $NH_4^+$ cation for $NR^1R^2R^3R^{4+}$), preferably a single substituent that represents hydrogen, or hydrocarbyl radicals that have 1 to 30 carbon atoms, for example alkyl groups that may or may not be saturated, cycloalkyl or aromatic groups, aryl or aralkyl groups, optionally substituted, comprising 1 to 30 carbon atoms.

The groups $R^1$, $R^2$, $R^3$, $R^4$, $R^5$ and $R^6$ can also represent hydrocarbyl radicals that carry one or more groups that are selected from among the groups —$CO_2R$, —C(O)R, —OR, —C(O)NRR', —C(O)N(R)NR'R", —NRR', —SR, —S(O)R, —$S(O)_2R$, —$SO_3R$, —CN, —N(R)P(O)R'R', —PRR', —P(O)RR', —P(OR)(OR'), —P(O)(OR)(OR'), in which the groups R, R' and R", identical or different, each represent hydrogen or hydrocarbyl radicals that have 1 to 30 carbon atoms.

The sulfonium and guanidium cations preferably correspond to one of the general formulas $SR^1R^2R^{3+}$ or $C(NR^1R^2)(NR^3R^4)(NR^5R^6)^+$, where the groups $R^1$, $R^2$, $R^3$, $R^4$, $R^5$ and $R^6$, identical or different, are defined as above.

The Q+ quaternary ammonium and phosphonium cations preferably correspond to one of the general formulas $NR^1R^2R^3R^{4+}$ and $PR^1R^2R^3R^{4+}$, or to one of the general formulas $R^1R^2N=CR^3R^{4+}$ and $R^1R^2P=CR^3R^{4+}$, in which $R^1$, $R^2$, $R^3$, and $R^4$, identical or different, are defined as above.

The Q+ ammonium and phosphonium cations can also be derived from nitrogen-containing and/or phosphorus-containing heterocycles comprising 1, 2 or 3 nitrogen atoms and/or phosphorus atoms, of the general formulas below:

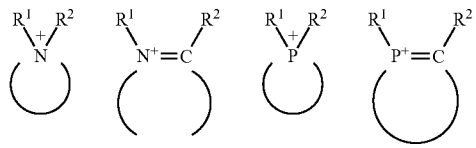

in which the cycles consist of 4 to 10 atoms, preferably 5 to 6 atoms, and $R^1$ and $R^2$, identical or different, are defined as above.

The Q+ quaternary ammonium and phosphonium cations can also correspond to one of the general formulas: $R^1R^{2+}N=CR^3—R^7—R^3C=N^+R^1R^2$ and $R^1R^{2+}P=CR^3—R^7—R^3C=P^+R^1R^2$, in which the groups $R^1$, $R^2$ and $R^3$, identical or different, are defined as above, and the group $R^7$ represents an alkylene or phenylene radical.

Among the groups $R^1$, $R^2$, $R^3$ and $R^4$, the following radicals will be mentioned: methyl, ethyl, propyl, isopropyl, primary butyl, secondary butyl, tert-butyl, butyl, amyl, phenyl or benzyl; the group $R^7$ can be a methylene, ethyl, propylene or phenylene group.

Preferably, the Q+ ammonium and phosphonium cations are selected from the group that is formed by N-butylpyridinium, N-ethylpyridinium, pyridinium, ethyl-3-methyl-1-imidazolium, butyl-3-methyl-1-imidazolium, hexyl-3-methyl-1-imidazolium, butyl-3-dimethyl-1,2-imidazolium, the (hydroxy-2-ethyl)-1-methyl-3-imidazolium cation, the (carboxy-2-ethyl)-1-methyl-3-imidazolium cation, the diethylpyrazolium, N-butyl-N-methylpyrrolidinium, N-butyl-N-methylmorpholinium, trimethylphenylammonium, tetrabutylphosphonium, and tributyl-tetradecyl-phosphonium.

By way of example of $Q^+A^-$ salts that can be used according to the invention, it is possible to cite butyl-3-methyl-1-imidazolium bis(trifluoromethylsulfonyl)amide, butylimidazolium triethylammonium bis(trifluoromethyl sulfonyl) amide, butyl-3-dimethyl-1,2-imidazolium bis(trifluoromethylsulfonyl)amide, N-butyl-N-methylpyrrolidinium bis(trifluoromethylsulfonyl)amide, butyl-3-methyl-1-imidazolium tetrafluoroborate, butyl-3-dimethyl-1,2-imidazolium, tetrafluoroborate, ethyl-3-methyl-1-imidazolium tetrafluoroborate, butyl-3-methyl-1-imidazolium hexafluoroantimonate, butyl-3-methyl-1-imidazolium trifluoroacetate, ethyl-3-methyl-1-imidazolium triflate, (hydroxy-2-ethyl)-1-methyl-3-imidazolium bis(trifluoromethylsulfonyl)amide, (carboxy-2-ethyl)-1-methyl-3-imidazolium bis(trifluoromethylsulfonyl)amide, N-butyl-N-methylmorpholinium bis(trifluoromethylsulfonyl)amide. These salts can be used by themselves or in a mixture.

Application in Catalysis

The suspension of metal nanoparticles in a non-aqueous ionic liquid that is thus defined is used, within the scope of the invention, as a catalytic composition in a process for hydrogenation of an aromatic feedstock.

The Feedstock or Substrate

The feedstock or substrate that can be hydrogenated in the hydrogenation process according to the invention is an aromatic feedstock that comprises monocyclic or polycyclic aromatic compounds and, more particularly in this latter case, compounds that have 2 or 3 condensed cycles, whereby said aromatic compounds can also comprise one or more O-, N- or S-type heteroatoms.

More particularly, the monocyclic aromatic compounds that are used in the hydrogenation process according to the invention are described by the general formulas C6H6-nAn in which n=1-3, and A represents a radical, such as hydrogen, a halogen, a nitrogen atom, a group —NO2, —CN, —CF3, —CH2C6H5, —R, OR, —C(O)R, C(R)2-C6H5, where R is a phenyl group or alkyl group with 1 to 6 carbon atoms.

By way of examples, it is possible to cite the aromatic compounds such as benzene, toluene, ortho-, meta- or para-xylenes, tetraline, alkyl-tetralines, alkyl-indanes, naphthalenes, or alkyl-naphthalenes, ortho-, meta- or para-cresols, anisole, acetophenone, chlorobenzene, styrene, ortho-, meta- or para-methylanisole, phenol, naphthalene and heteroaromatic compounds such as pyridine, 2,3,4-picolines, furan, benzofuran, thiophene, benzothiophene, quinoline, n-methylindole and triazine.

The compounds that are to be hydrogenated can be taken by themselves or in a mixture, pure or dilute, generally by at least one alkane, such that they are found in petroleum "fractions," for example fractions that are obtained from the distillation of crude petroleum (distillation under vacuum or under atmospheric pressure), and various conversion processes such as the fractions that are obtained from catalytic cracking and catalytic hydrocracking processes.

The Hydrogenation Reaction

The hydrogenation reaction can be conducted in a closed system, in a half-open system, or continuously with one or more reaction stages. Vigorous stirring should ensure good contact between the reagent or reagents and the suspension of metal nanoparticles in the ionic liquid that acts as a catalytic composition.

The hydrogenation reaction can be conducted with a multiphase mixture (gas/liquid/liquid or gas/liquid). The suspension of metal nanoparticles in the ionic liquid can be separated from products by decanting and/or by extraction. It can be at least partially recycled and reused directly without intermediate treatment in the reaction phase. It is also possible to add fresh catalytic composition to remedy accidental losses or drops in performance levels.

The operating conditions of the hydrogenation reaction are as follows:
  The reaction temperature is between 0° C. and 250° C., preferably between 20° C. and 150° C., and more preferably between 20 and 100° C. It is possible to operate above or below the melting point of the non-aqueous ionic liquid medium, whereby the dispersed solid state is not a limitation to the good course of the reaction.
  The hydrogen pressure is between 0.1 and 20 MPa, preferably between atmospheric pressure and 5 MPa.
  The molar ratio of substrate to metal is between 1 and 10,000, and preferably between 1 and 1,000.

It is important to note that it is well known to one skilled in the art that the reaction for hydrogenating aromatic compounds is more difficult to catalyze than the reaction for hydrogenating olefins. This results from the stabilization energy level that it is necessary to reach when the hydrogenation reaction brings about the loss of aromaticity. (See J. March, Advanced Organic Chemistry: Reaction, Mechanisms, and Structure, 4$^{th}$ Ed., Wiley-Interscience, New York, 1992, page 780).

One preferred embodiment of the process for hydrogenating an aromatic feedstock according to the invention implements a metal nanoparticle suspension in at least one non-aqueous ionic liquid that is selected from among butyl-1-methyl-3-imidazolium hexafluorophosphate [BMI][PF$_6$], butyl-1-methyl-3-imidazolium tetrafluoroborate [BMI][BF$_4$], and butyl-1-methyl-3-imidazolium bis-trifluoromethylsulfonyl amide [BMI][NTf$_2$], in which said metal nanoparticles comprise at least one transition metal in the zero-valence state, whereby the transition metal is selected from among rhodium and ruthenium, taken by themselves or in a mixture, and in which said metal nanoparticles are in contact with a nitrogen-containing ligand that is selected from among 2,2'-bipyridine and 2,2,4-tris-(2-pyridyl)-triazine or TPST.

EXAMPLES

The following examples illustrate the invention without limiting its scope.

Abbreviations that are Used

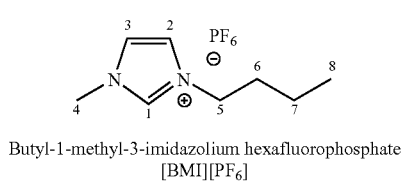

Butyl-1-methyl-3-imidazolium hexafluorophosphate
[BMI][PF$_6$]

IL: Non-aqueous ionic liquid
Bpy: 2,2'-bipyridine

Example 1

Synthesis of Rh Nanoparticles in the Zero-Valence State Rh(O) by Chemical Reduction Using a Hydride as a Reducing Agent in the Ionic Liquid [BMI][PF$_6$].

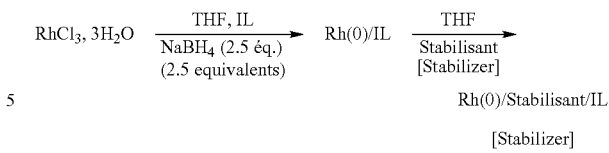

The suspension of metal nanoparticles of rhodium in the ionic liquid [BMI][PF$_6$] is prepared at 20° C. 10 mg ($3.8 \cdot 10^{-5}$ mol) of RhCl$_3$, 3H$_2$O is brought into solution in a mixture of THF (5 ml)/ionic liquid [BMI][PF$_6$] (2 ml). 3.6 mg (9.5 mol/2.5 equivalents) of NaBH$_4$ reducing agent, brought into solution in a minimum of water, is then added quickly to the mixture, while being stirred vigorously, at ambient temperature. Without waiting, 2.9 mg ($1.9 \times 10^{-5}$ mol, 0.5 equivalent/metal) of 2,2'-bipyridine ligand, solubilized in 5 ml of tetrahydrofuran solvent or THF, is added, while being stirred vigorously, to the reaction mixture. The THF is then evaporated under reduced pressure, and the suspension of metal nanoparticles of rhodium is kept under vacuum and stirred vigorously for 2 hours.

The size distribution of the nanoparticles has a Gaussian form centered on 1.55 nm.

Example 2

Synthesis of Rhodium Nanoparticles in the Zero-Valence State Rh(O) by Chemical Reduction Using Molecular Hydrogen in the Ionic Liquid [BMI][PF$_6$].

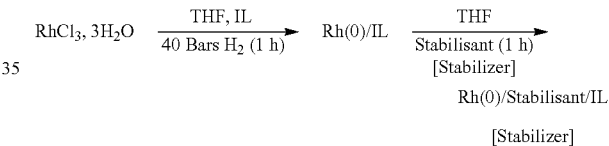

The suspension of metal nanoparticles of rhodium in the ionic liquid [BMI][PF$_6$] is prepared at 20° C. 10 mg ($3.8 \cdot 10^{-5}$) of RhCl$_3$, 3H$_2$O is brought into solution in a mixture of THF (5 ml)/ionic liquid [BMI][PF$_6$] (2 ml). The whole is placed under vigorous stirring at ambient temperature and under 40 bar of molecular hydrogen H$_2$ in an autoclave. At the end of 1 hour, 2.9 mg ($1.9 \times 10^{-5}$ mol, 0.5 equivalent/metal) of 2,2'-bipyridine ligand that is solubilized in 5 ml of THF solvent is added to the mixture while being stirred vigorously with the reaction mixture. The reaction mixture is then placed again under vigorous stirring at ambient temperature and under 40 bar of H$_2$. At the end of 1 hour, the reaction is stopped, and the THF is evaporated under reduced pressure. The suspension of metal nanoparticles of rhodium that is obtained is then dried under vacuum, and vigorous stirring is maintained for 2 hours.

The size distribution of the nanoparticles has a Gaussian form that is centered on 2.33 nm.

Example 3

Synthesis of Ruthenium Nanoparticles in the Zero-Valence State Ru(0) by Chemical Reduction Using a Hydride as a Reducing Agent in the Ionic Liquid [BMI][PF$_6$].

The suspension of metal nanoparticles of ruthenium in the ionic liquid [BMI][PF$_6$] is prepared at 20° C. 7.9 mg ($3.8 \cdot 10^{-5}$ mol) of RuCl$_3$, 3H$_2$O is brought into solution in a mixture of THF (5 ml)/ionic liquid [BMI][PF$_6$] (2 ml). Then, 3.6 mg (9.5·10⁻⁵ mol; 2.5 equivalents) of reducing agent NaBH$_4$, brought into solution in a minimum of water, is added to the mixture quickly and while being stirred vigorously. Immediately afterward, 2.9 mg (1.9×10⁻⁵ mol, 0.5 equivalent/metal) of 2,2'-bipyridine ligand, solubilized in 5 ml of THF, is added quickly and while being stirred vigorously to the reaction mixture. The THF is then evaporated under reduced pressure, and the suspension of metal nanoparticles of ruthenium that is obtained is dried under vacuum and vigorous stirring is maintained for 2 hours.

The size distribution of the nanoparticles is between 1.55 and 2.5 nm.

Example 4

General Procedure for Hydrogenation Under Pressure of Molecular Hydrogen 2 ml of a suspension of metal nanoparticles of rhodium in the ionic liquid [BMI][PF$_6$] that is prepared according to Example 1 and 100 equivalents/metal of substrate to be hydrogenated are introduced into a stainless steel autoclave that is equipped with a magnetic rod. The autoclave is then purged 4 times with hydrogen, the temperature is set at 80° C., and then the hydrogen pressure is set at 4 MPa. The reaction starts up with the beginning of the stirring. The progression of the reaction is tracked by GPC [gas phase chromatography]. At the end of the reaction, the catalytic system is dispersed into 10 ml of acetonitrile CH$_3$CN, centrifuged for 10 minutes (15,300 rpm⁻¹; 20° C.). The sample is then analyzed by GPC.

Example 5

Influence of the Quantity of 2-2' Bipyridine Ligand. Application to the Hydrogenation of Styrene at 80° C., 4 Mpa.

The suspension of metal nanoparticles of rhodium in the ionic liquid [BMI][PF$_6$] is produced as described in Example 1, except that the quantity of 2-2' bipyridine ligand that is introduced during the synthesis is made to vary. The catalytic tests are carried out as described in Example 4. The results are combined in Table 1.

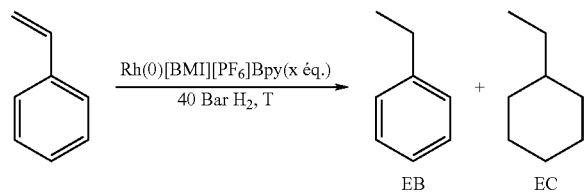

TABLE 1

Influence of the quantity of 2-2' bipyridine on the catalytic activity at 80° C., 4 MPa.

| 2,2'-Bipyridine/Rh Equivalents | Product (% by Weight) | Conversion (%) |
|---|---|---|
| 0.2 | EB (0) + EC (100) | 100 |
| 0.4 | EB (5) + EC (95) | 100 |
| 0.5 | EB (40) + EC (60) | 100 |

Conditions: Catalyst: Rh(O)[BMI][PF$_6$] (2 ml), T = 80° C., 4 MPa of H$_2$, [styrene]/[Rh] = 100 mol; EB = ethylbenzene, EC = ethylcyclohexane, t = 15 h

Example 6

For Comparison: Use of a Ligand from the Family of Phenanthrolines

Under the same conditions as Example 4, a test was carried out with the combination of palladium and ligand from the family of phenanthrolines on styrene, with a phenanthroline/Pd molar ratio of 0.5.

The results are provided in Table 2 below:

TABLE 2

| Phenanthroline/Pd Equivalents | Product (% by Weight) | Conversion (%) |
|---|---|---|
| 0.5 | EB (95) + EC (5) | 100 |

Conditions: Catalyst: Pd (O)[BMI][PF$_6$] (2 ml), T = 80° C., 4 MPa of H$_2$, [styrene]/[Pd] = 100 mol; EB = ethylbenzene, EC = ethylcyclohexane, t = 15 h The results of the test show that the use of the phenanthroline ligand, in combination with the palladium, leads to conversions of ethylcyclohexane (EC) that are quite inferior to those obtained with a ligand other than the phenanthroline under the same conditions.

Example 7

Influence of the Nature of the Ionic Liquid Used in the Synthesis of the Suspension of Nanoparticles of Rh(O). Application to the Hydrogenation of Styrene (4 MPa of Hydrogen Pressure and 80° C.).

The suspension of metal nanoparticles of rhodium in ionic liquid [BMI][PF$_6$] is carried out as described in Example 1, except that the nature of the ionic liquid that is used during the synthesis is made to vary. The catalytic tests are carried out as described in Example 4.

TABLE 3

Influence of the Counter-Anion on the Catalytic Activity (P = 4 MPa, T = 80° C.)

| Ionic Liquid | Product (%) | Conversion (%) |
|---|---|---|
| [BMI][PF$_6$] | EB (40) + EC (60) | 100 |
| [BMI][BF$_4$] | EB (8) + EC (92) | 100 |
| [BMI][NTf$_2$] | EB (60) + EC (40) | 100 |
| [HEA][NTf$_2$] | EB (45) + EC (55) | 100 |
| [MBPyrr][NTf$_2$] | EB (70) + EC (30) | 100 |

Conditions: catalyst: Rh(O)IL (2 ml) 2,2'-bipyridine (0.5 equivalent),
T = 80° C., 4 MPa of H$_2$, [styrene]/[Rh] = 100, t = 15 h,
EB = ethylbenzene,
EC = ethylcyclohexane,
BF$_4$ = tetrafluoroborate
NTf$_2$ = bis-trifluoromethylsulfonyl amide
MBPyrr = N,N'-methyl-butyl-pyrrolidinium
HEA = N,N-dimethyl-N-dodecyl-N-(hydroxyethyl)ammonium

Example 8

Effect of the Nature of the ligand. Application to the Hydrogenation of the Styrene (4 MPa of Hydrogen Pressure and 80° C.)

The suspension of metal nanoparticles of rhodium in the ionic liquid [BMI][PF$_6$] is carried out as described in Example 1, except that the nature of the ligand that is used during the synthesis is made to vary. The catalytic tests are carried out as described in Example 4.

TABLE 4

Influence of the ligand on the catalytic activity

| Ligand | Product (% by Weight) | Conversion (%) |
|---|---|---|
| 2-2' Bipyridine | EB (40) + EC (60) | 100 |
| TPST | EB (6) + EC (94) | 100 |
| TPPZ | EB (71) + EC (29) | 100 |

Conditions: Catalyst: Rh(O)[BMI][PF$_6$](2 ml) ligand (0.5 equivalent),
T = 80° C., 40 bar of H$_2$, [styrene]/[Rh] = 100, t = 15 h,
EB = ethylbenzene,
EC = ethylcyclohexane,
TPST = 2,4,6-tris-(2-pyridyl)-triazine
TPPZ = tetra-2-pyridinyl-pyrazine

Example 9

Effect of the Nature of the Ligand (Pyridine)

The suspension of metal nanoparticles of rhodium in the ionic liquid [BMI][PF$_6$] is carried out as in Example 1, except that the pyridine is used as a ligand instead of bipyridine, and the ligand/metal molar ratio is set at 0.5. The catalytic test is carried out as in Example 4. The styrene is completely converted into ethylcyclohexane at the end of 15 hours.

Example 10

Recycling of the Catalytic System

The suspension of metal nanoparticles of rhodium in the ionic liquid [BMI][PF$_6$] is carried out as described in Example 1. The catalytic tests are carried out as described in Example 5. 395.7 mg (3.8·10$^{-3}$ mol, 100 equivalents) of styrene is added to 2 ml of the suspension Rh(O)[BMI][PF$_6$]/Bpy (0.5 equivalent). The whole is placed under vigorous stirring, at 80° C. and 40 bar of hydrogen. The reaction kinetics is followed by gas phase chromatography (GPC), by analysis of a sampling of the reaction medium. At the end of the reaction, the extraction of the products is carried out with diethyl ether (5 ml). This extraction stage is carried out as many times as necessary until the reaction products of the ionic liquid phase are eliminated. The organic phases that are extracted are combined and analyzed by GPC. The suspension of nanoparticles is dried under vacuum for 2 hours while being stirred vigorously and reused in a second catalytic test.

In each case, the styrene is completely converted. At the end of the 2$^{nd}$ cycle, a 50/50 mixture of ethylbenzene and ethylcyclohexane is obtained within 15 hours.

The suspension of the nanoparticles in the ionic liquid remains perfectly stable. No metal deposit is observed.

The invention claimed is:

1. In a process comprising catalytically hydrogenating an aromatic feedstock, the improvement wherein the catalyst comprises a suspension of metal nanoparticles of a mean size of between 1 and 20 nanometers, and at least one non-aqueous ionic liquid that is selected from among butyl-1-methyl-3-imidazolium hexafluorophosphate [BMI][PF6], butyl-1-methyl-3-imidazolium tetrafluoroborate [BMI][BF4], and butyl-1-methyl-3-imidazolium bis-trifluoromethylsulfonyl amide [BMI][NTf2], in which said metal nanoparticles comprise at least one transition metal in the zero-valence state, wherein the transition metal is selected from among rhodium and ruthenium, taken by themselves or in a mixture, and in which said metal nanoparticles are in contact with a nitrogen-containing ligand that is selected from among 2-2' bipyridine, pyridine and 2,4,6-tris-(2-pyridyl)-s-triazine (TPST).

2. A process for hydrogenation of aromatic compounds according to claim 1, in which said transition metal is rhodium.

3. A process for hydrogenation of aromatic compounds according to claim 1, in which said transition metal is ruthenium.

4. A process for hydrogenation of aromatic compounds according to claim 1, in which the aromatic feedstock comprises monocyclic or polycyclic aromatic compounds, said compounds optionally comprising one or more heteroatoms from O, N or S.

5. A process for hydrogenation of aromatic compounds according to claim 1 comprising a reaction temperature between 0° C. and 250° C., a hydrogen pressure between 0.1 and 20 MPa, and a molar ratio of the aromatic feedstock to metal between 1 and 10,000.

6. A process according to claim 5 wherein the molar ratio is between 1 and 1,000.

7. A process for hydrogenation of aromatic compounds according to claim 1, in which said metal nanoparticle suspension is obtained by chemical reaction by bringing into contact, followed by stirring, of a metal precursor, a reducing agent, at least one of said ionic liquids, and at least one of said nitrogen-containing ligands, wherein the addition of different components can be done in any order.

8. A process for hydrogenation of aromatic compounds according to claim 7, in which the addition of the nitrogen-containing ligand is done in a second stage following a first stage of bringing into contact the metal precursor, the reducing agent and at least one ionic liquid.

9. A process according to claim 1, wherein the aromatic feedstock comprises styrene, the metal nanoparticles comprise rhodium in the zero state, and the non-aqueous ionic liquid comprises at least one of [BMI] [PF6] or [BMI] [BF4] and the nitrogen-containing ligand comprises at least one of 2,2'bipyridine or TPST.

10. A process according to claim 9, wherein the non-aqueous ionic liquid comprises [BMI] [PF6] and the nitrogen-containing ligand comprises 2,2'bipyridine in a ratio on the order of about 0.2 to 0.4 equivalents to 1.0 equivalent of rhodium.

* * * * *

UNITED STATES PATENT AND TRADEMARK OFFICE
CERTIFICATE OF CORRECTION

PATENT NO. : 8,389,783 B2  
APPLICATION NO. : 12/597260  
DATED : March 5, 2013  
INVENTOR(S) : Leger et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 511 days.

Signed and Sealed this

First Day of September, 2015

Michelle K. Lee
*Director of the United States Patent and Trademark Office*